(12) United States Patent
Mottier et al.

(10) Patent No.: US 6,545,278 B1
(45) Date of Patent: Apr. 8, 2003

(54) GAS DISCRIMINATING GAS DETECTOR SYSTEM AND METHOD

(75) Inventors: François Mottier, Stamford, CT (US); Scott Bruce, Montvale, NJ (US)

(73) Assignee: Delphian Corporation, Northvale, NJ (US)

( * ) Notice: Subject to any disclaimer, the term of this patent is extended or adjusted under 35 U.S.C. 154(b) by 0 days.

(21) Appl. No.: 09/298,595

(22) Filed: Apr. 23, 1999

(51) Int. Cl.[7] ................................................ G01J 3/42
(52) U.S. Cl. ............................. 250/339.13; 250/339.12
(58) Field of Search ..................... 250/339.13, 339.12, 250/341.1, 341.5, 343

(56) References Cited

U.S. PATENT DOCUMENTS

| | | | |
|---|---|---|---|
| 3,781,838 A | 12/1973 | Primmer | 340/237 S |
| 3,927,555 A | 12/1975 | Godwin et al. | 73/23 |
| 4,365,303 A | * 12/1982 | Hannah et al. | 702/28 |
| 5,014,217 A | * 5/1991 | Savage | 702/28 |
| 5,023,804 A | 6/1991 | Hoult | 356/319 |
| 5,081,998 A | 1/1992 | Yelderman et al. | 128/719 |
| 5,320,733 A | 6/1994 | Böhm | 204/408 |
| 5,418,366 A | 5/1995 | Rubin et al. | 250/338.5 |
| 5,429,805 A | 7/1995 | Uno et al. | 422/83 |
| 5,448,070 A | 9/1995 | Day et al. | 250/339.13 |
| 5,497,003 A | 3/1996 | Baliga et al. | 250/338.3 |
| 5,510,269 A | 4/1996 | Black et al. | 436/164 |
| 5,583,339 A | 12/1996 | Black et al. | 250/339.13 |
| 5,591,975 A | 1/1997 | Jack et al. | 250/338.5 |
| 5,610,400 A | 3/1997 | Weckstrom | 250/345 |

* cited by examiner

*Primary Examiner*—Georgia Epps
*Assistant Examiner*—Richard Hanig
(74) *Attorney, Agent, or Firm*—Fitch, Even, Tabin & Flannery

(57) ABSTRACT

A gas detection system and method are provided for determining the type of gas present and the concentration of the gas in terms of a percentage of a specific level of the gas. This percentage level may be in terms of a lower explosive limit level of a combustible gas. The system generally includes a testing chamber, a detection channel apparatus, a memory for storing a plurality of gas signature tables, and a programmed controller for determining the identity and concentration level of a gas. The system and method further provide for the accurate determination of gas concentration level at very high and low concentration levels by weighted average computation.

35 Claims, 4 Drawing Sheets

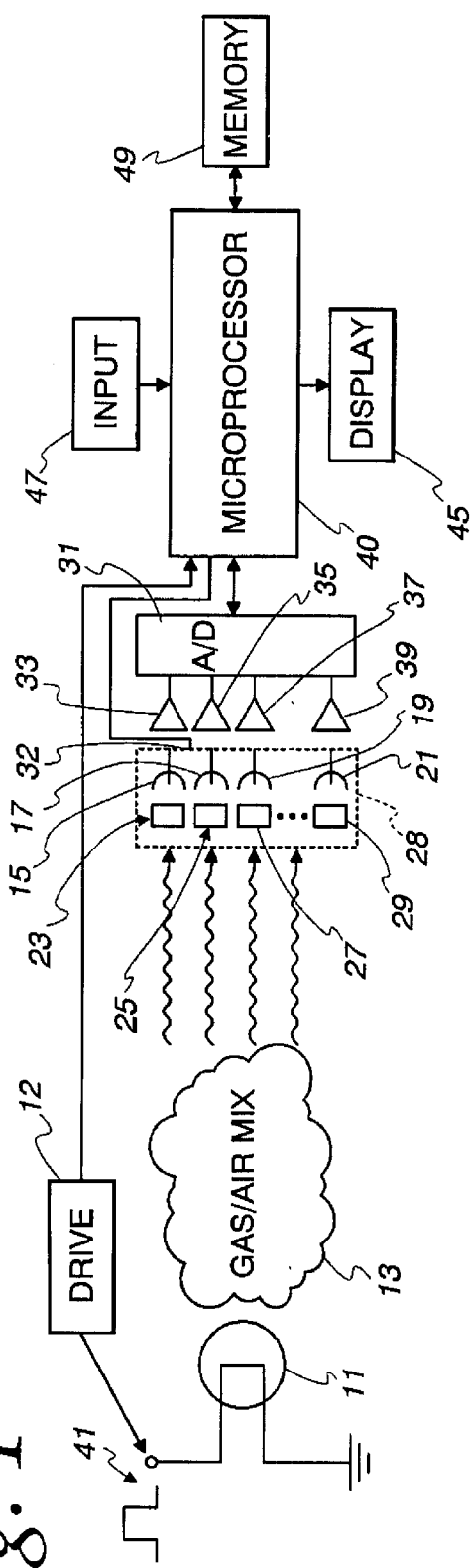
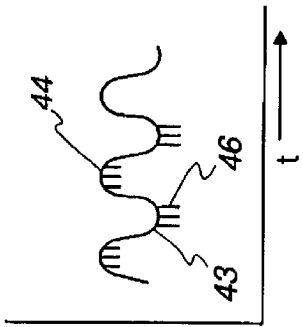
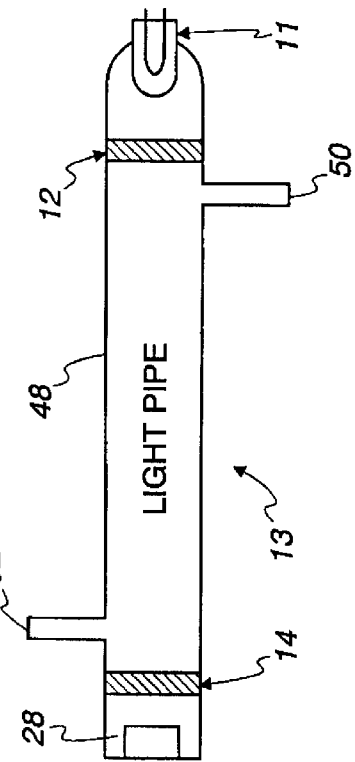
Fig. 1
Fig. 3
Fig. 2

| % LEL | 3.25 μm ① | 3.35 μm ② | 3.4 μm ③ |
|---|---|---|---|
| 0 | 0.0000 | 0.0000 | 0.0000 |
| 25 | 0.0030 | 0.0665 | 0.0785 |
| 50 | 0.0049 | 0.1423 | 0.1628 |
| 100 | 0.0092 | 0.2932 | 0.3209 |
| 500 | 0.0409 | 0.5870 | 0.5565 |

| | MEASURED ABSORPTION | Δa | ΔLEL | W |
|---|---|---|---|---|
| ① 3.25 μm CHANNEL | 0.005 | 0.0092-0.0049= 0.0053 | 100-50=50 | 0.0053/50=0.0001 |
| ② 3.35 μm CHANNEL | 0.142 | 0.1423-0.0665= 0.0758 | 50-25=25 | 0.0758/25=0.00303 |
| ③ 3.40 μm CHANNEL | 0.163 | 0.3209-0.1628= 0.1581 | 100-50=50 | 0.1581/50=0.003163 |

| ALTITUDE (FT) | 50% LEL CAL GAS READS AS | CORRECTION FACTOR |
|---|---|---|
| -6000 | 62% | 0.81 |
| -4000 | 58% | 0.87 |
| -2000 | 54% | 0.93 |
| 0 | 50% | 1.00 |
| 2000 | 48% | 1.08 |
| 4000 | 43% | 1.16 |
| 6000 | 40% | 1.25 |
| 8000 | 37% | 1.35 |
| 10000 | 34% | 1.45 |
| 12000 | 32% | 1.57 |
| 14000 | 29% | 1.70 |
| 16000 | 27% | 1.84 |
| 18000 | 25% | 2.00 |
| 20000 | 23% | 2.17 |

GAS DISCRIMINATING GAS DETECTOR SYSTEM AND METHOD

BACKGROUND OF THE INVENTION

The present invention relates to gas detection systems based on measurement of absorption of electromagnetic radiation by the gas of interest, and particularly to such systems which identify the type of gas present and which measure the concentration of the gas of interest in terms of percentage of a specific level of such gas in ambient air. Such specific level may be the lower explosive limit level of a combustible gas, or the maximum safe level for eight hour exposure by humans to a toxic gas.

In the following description the term "optical" will be understood to signify relating to electromagnetic radiation anywhere in the spectrum between the long microwave frequencies and the ultraviolet radiation of less than 100 nm. "Light" will be understood as any form electromagnetic flow of energy.

All gases which are the subjects of optical detection are known to exhibit attenuation of radiation in portion of the electromagnetic spectrum. Optical gas detection systems for such gases generally comprise one or more source(s) of electromagnetic radiation which direct their output through a gas to be identified to one or more light detectors. The detectors each respond to a small portion of the electromagnetic spectrum and electrical output levels from the detectors can be used to measure light-attenuation to identify the presence of a particular gas. Although, some success has been achieved in creating such optical gas detectors, they tend to be incapable of distinguishing between similar gases of the same class of gases, such as distinguishing between methane and butane, both of which are hydrocarbon gases. In many cases it is desirable to know not only that gases are present but whether the concentration of such gases are near a limit which might cause a problem. For example, when a hydrocarbon gas may be present it would be desirable to know if the gas concentration is at or near the level at which an explosion might occur. This limit is referred to herein as the lower explosive limit level or LEL level.

With known detectors it is possible to detect the presence of hydrocarbon gases by measuring the attenuation of infrared (IR) light in a detector as described above. Without knowing a priori which hydrocarbon gas or vapor is present, it is not possible to indicate the concentration of gas present or whether the detected IR attenuation may indicate a possibly explosive mixture or not.

The industrial environment also creates problems relating to continuous sampling of changing sampled air. That is, how can suspect air be substantially continuously evaluated by a detector in an industrial environment and still be expected to achieve the necessary gas discrimination and accuracy in lower explosive limit level detection.

SUMMARY OF THE INVENTION

The above problems are solved and an advance is achieved in accordance with the present invention. As disclosed herein, an apparatus for detecting and measuring concentration of gases comprises a chamber containing an air/gas mixture to be tested and one or more light sources for directing. light through the air/gas mixture to one or more light detectors. The light source(s) and detector(s) are used as described hereinafter to define a plurality of detection channels each for responding to a specific band of the light spectrum. The apparatus may also include a reference channel which is similar to the detection channels but responds to a light band which normally does not exhibit attenuation for the gases expected. Output signals from the detectors are sampled by a controller and used to measure the absorption by the air/gas mixture of light in the bands individually associated with the detection channels. The apparatus is preprogrammed with a signature table for each gas expected. Each signature table stores values representing expected output signals in the detection channels for a plurality of concentrations of the gas represented by the table. When three detection channels are used by the apparatus, each gas signature table will include three sets of entries, one for each detection channel, corresponding to each of a plurality of concentrations of the gas represented by the table.

The controller regularly samples the output signals in the detection and reference channels and normalizes the signals to render them independent of variations in hardware characteristics due to production fluctuations, and to render them independent to variations due to aging of the equipment and compensation of temperature effects. A first normalization is obtained by dividing each detection and reference channel output signal by the value of the same channel when the gas detection apparatus was presented with an atmosphere devoid of any of the gases to be detected, resulting in a normalized detector channel signal. A second normalization is obtained by dividing each normalized detection channel signal by the normalized reference channel signal.

After normalization, the controller compares the detection channel signal values to the various expected signal values of the signature tables. In one embodiment, such comparison is done by selecting a possible candidate gas contained in the signature tables, reading its signature table and computing from the signature table the gas concentration for each of the signal values using standard interpolation. If the multiple gas concentrations thus calculated do not match each other the selected candidate gas is different from the gas present in the test, and a next gas in the signature tables is selected to repeat the calculation. If the multiple gas concentrations thus calculated do match each other the selected candidate gas is the gas present in the test, and the concentration of the gas is the concentration calculated from the signature table. As long as a substantial match is not detected in a candidate signature table, other gas signature tables are checked one at a time. If none of the gas signature tables furnish a substantial match a default gas signature table is used to force a gas concentration reading. Advantageously, the signature tables may be grouped in accordance with a common characteristic so that some tables may be excluded based on the sampled detection channel output signals. For example, when three detection channels numbered 1, 2 and 3 are used, the detection channel signals are compared with one another and arranged in ascending order of detected absorption. Beforehand, the signature tables are also grouped according to ascending order of expected absorption, and only signature tables having the same characteristics as the detection channel output signals are compared with the detection channel output signals. In the example using detection channels 1, 2 and 3, their output signals, arranged by ascending absorption may be 3-1-2. These detection channel output signals are compared only to signature tables having expected output signals arranged in the 3-1-2 sequence.

In an embodiment of the gas detection and measurement system a weighted average of the concentration identified from the signature tables is computed. The weighted average computation is particularly valuable in measurements which are very close to the detection limits of one of the detection channels and in situations where a significant change in gas concentration does not cause a significant change in measured infrared absorption. The last named situation may occur, for example, at very low concentrations of gas and at high concentrations. In the weighted average computation, a concentration level is identified for the signal output of each of a plurality of detection channels. The identified concentration levels are each multiplied by a weighting factor representing the change of absorption per change in gas concentration, and an average is computed by dividing the sum of the weighted concentration by the total of the weighting factors. This method reduces the influence on the final measured concentration of infrared absorption readings which may not be representative.

The apparatus may be constructed as a controller unit including a processor, display and input device and a changeable measuring head. The measuring head may include the light sources and detectors to define the detection channels and a persistent memory such as EPROM to store signature tables and normalizing values for gases expected to be detected by that particular measuring head. With this construction the system can be reconfigured for testing for different sets of gases by simply changing the measuring head.

BRIEF DESCRIPTION OF THE DRAWINGS

The embodiments of the present invention are described relative to the following drawings wherein:

FIG. 1 shows a block diagram of the apparatus for carrying out the present invention;

FIG. 2 shows an embodiment of the light source, gas collector and detector;

FIG. 3 shows a representative signal from a detector of FIG. 1;

DETAILED DESCRIPTION OF PREFERRED EMBODIMENT

Figures 4, 5, 6:
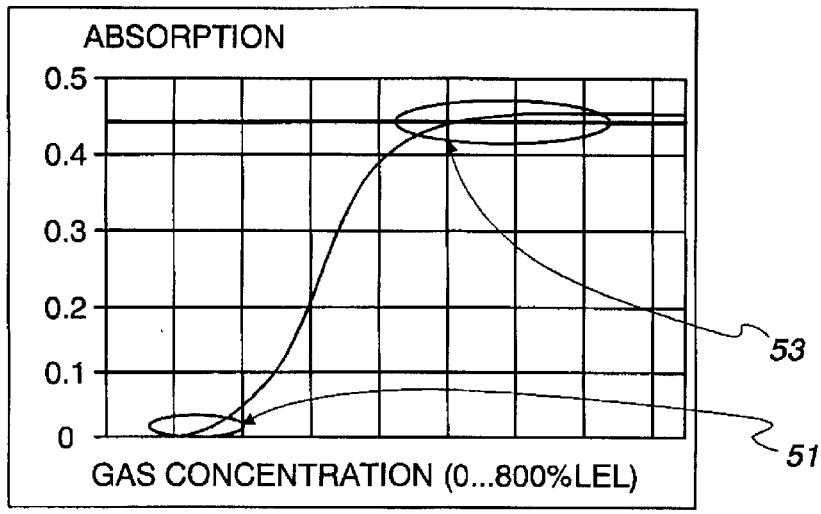
FIG. 4 represents a gas signature table.
FIG. 5 represents LEL average calculation in an example of an analysis routine.
FIG. 6 illustrates an example of possible inaccuracies with light absorption detection.

The embodiment of FIG. 1 shows a light source 11 for directing light through a test gas/air mix represented as 13 to four detectors 15, 17, 19, 21. The detectors are from time to time referred to collectively as 28. In the present embodiment the light source creates light in the infrared band and the detectors detect portions of that band. In other embodiments light in any portion of the electromagnetic spectrum may be used. The detectors of the present embodiment comprise thermopiles, as are well known in the art, but could also be other types of detectors such as photo resistors, photovoltaic cells, pyroelectric detectors or the like, as appropriate to the light wavelength used. Each detector receives IR power from source 11 via a respective individual optical filter 23, 25, 27 and 29. The center frequency and bandwidth of the optical filters 23–29 is predetermined to limit the input to individual portions of the IR band which are meaningful for detecting and measuring expected target gases. In the present embodiment, which is intended to detect hydrocarbons, filter 23 defines a 0.04 micron wavelength channel around 3.25 micron, filter 25 defines a 0.04 micron wavelength channel around 3.35 micron, filter 27 defines a 0.04 micron wavelength channel around 3.4 micron and filter 29 defines a 0.04 micron wavelength channel around 3.0 micron. The output signal of each detector represents optical transmission in a detection channel. It should be mentioned that in other embodiments the width of the pass band or the center frequency of a filter may vary from that described.

The physical arrangement of light source 11, air gas mixture 13 and the detectors is shown in FIG. 2. In the arrangement of FIG. 2, gas is caused to enter a chamber 48 via an inlet 50 and exit the chamber at an outlet 52. The entry and exit. of gas may be caused by forcing gas into inlet 50, drawing gas from outlet 52 or creating convection flow within the chamber 48. The light from source 11 passes through the mixture in chamber 48 to the detector 28 and signals from the detector are measured as described herein to detect attenuation of the light by the mixture. The combination of chamber 48, light source 11 and detectors 28 is built as a non-imaging device so that substantially equal energy can be applied uniformly at the detector. In some instances, due for example to the dimension of the system non-uniform energy may occur at the detectors. Such non-uniformity may be reduced by mechanical roughness on the inner walls of the chamber, frosting the envelope of the light source or, as shown in FIG. 2 at 12 and 14, diffusers near the source or detectors, or both. PTFE in a thickness of from 10 micron to 5.0 mm has been found to provide effective diffusion.

Electrical output signals from each detector 15–21 (FIG. 1) which represent light transmission in detection channels are connected to a multiplexed analog to digital converter 31 via a respective amplifier 33, 35, 37 and 39. A microprocessor 40 periodically interrogates A/D converter 31 to repetitively read out digital values representing the electrical signals from each of the detectors 15–21. Light source 11 is shown as an incandescent source, however, any such source with wide optical bandwidth emission, capable of rapidly being turned on and off could be used, as could light sources which are mechanically, electro-optically, or otherwise chopped. Light source 11 is energized by a continuing rectangular wave, represented at 41, to repetitively turn on and off. The on and off cycles of light source 11 result in a recurring sequence of peak light/minimum light impulses being applied to the detectors 15–21. FIG. 3 represents the output signals from a detector and shows the response of the detector to the recurring pulses of received light.

Microprocessor 40 interrogates the A/D converter 31 at a sufficient rate so that at least the peaks and minimums of the detector signals are identified. In the present embodiment light source 11 is pulsed in synchronism with the sampling by the microprocessor which controls the on-off rate of the light source via a driver 12. Microprocessor 40 samples the output of each detector at multiple times near the center of each detector signal maximum and minimum to average the noise in the signal. In other embodiments the light pulsing and sampling by A/D converter could be unsynchronized with the sampling occurring sufficiently rapidly to detect all maximum and minimum detector values.

Microprocessor 40 is a preprogrammed device which samples the output signals from detectors 15–21, analyzes those signals to detect and measure light absorption by gases and vapors 13, and controls a display 45 to identify gases detected and the concentrations of the gases detected. Microprocessor 40 is connected to a memory 49 having a plurality of memory locations for storing the program and data used in the present system. At any given time during operation memory 49 stores in separate registers a value representing the present output of each of the detectors. In the present embodiment, four such registers exist, each for storing the output of a different detector 15, 17, 19 and 21. The values stored to represent the present output of a detector, e.g. 15, are computed by subtracting a minimum value, e.g. 43, from an adjacent peak value, e.g. 44.

Microprocessor 40 includes a start-up and normalization routine which is initiated automatically during the power on self test (POST), or through intervention by a user from an input unit 47. During the start-up and normalizing routine, the microprocessor system is initialized as is well known and certain normalizing values are recorded. The normalizing values, which advantageously may be stored in persistent memory such as EPROM or EEPROM, are used to normalize the value of later samples for computation. Accordingly, the normalizing routine should be performed when the gas air mix 13 consists only of "clean" air without any of the gases which are to be detected, or which attenuate any of the plurality of wavelengths determined by the filter/detector combinations. These normalizing values are collected and calculated (peak minus minimum) as are other values but they are not changed during normal operation. In the present embodiment, the normalizing values are referred to as $Ao^1, Ao^2, Ao^3, Ao^4$, with each representing a collected signal from a respective one of the four detectors 15, 17, 19 and 21.

Before a sampled value computed for a detector is used to replace the present value for that detector stored in memory 49, the two values are compared to identify any difference between the two. When a difference of about 1 part in one thousand or more in attenuation is detected, an analysis routine is entered in an attempt to identify a gas in the air/gas mixture 13, which has caused this attenuation change. In the analysis routine the present value $A^K$ for each detector is divided by the normalizing value for that detector to produce a first normalized value. Thus, the first normalized value for a given detector is $$a_K = A^K/A_o^K$$

The first normalizing of values ensures that variations in sensitivity are compensated for automatically. After first normalizing the first normalized values for each detection channel is divided by the first normalized reference channel value. This is the second normalizing step. The second normalized values for the detection channels are used by the analysis routine for further processing.

The filters 23, 25, 27 and 29 and detectors 15, 17, 19 and 21 define four channels substantially centered at 3.25 micron, 3.35 micron, 3.4 micron and 3.0 micron. The 3.0 micron channel is outside of the absorption band of most hydrocarbons and is used primarily as a reference channel. The remaining channels comprise detection channels. In the present embodiment the gases of interest exhibit a signature represented by the absorption values at the tested wavelength of the 3.25 micron, 3.35 micron and 3.4 micron channels. For example, ethane exhibits attenuation only in the 3.35 micron and 3.4 micron bands with a ratio of about 3 to 2; propane exhibits absorption in the 3.35 micron and 3.4 micron bands but the ratio is about 1 to 3; cyclohexane exhibits absorption exclusively in the 3.4 micron channel; butane exhibits absorption in only the 3.35 and 3.4 micron bands at a ratio of about 1 to 8; bivinyl exhibits absorption at all three test channels at a ratio of 8 to 6 to 1, and methane exhibits substantially equal attenuation in all three channels. During the design and fabrication stage of the present embodiment, tests are performed on each gas of interest using the disclosed apparatus and signature tables are prepared to represent attenuation by each gas at a plurality of different concentrations. FIG. 4 represents one such signature table. It should be mentioned that the gas signature tables may include signature values for more concentration levels than shown in FIG. 4. It should also be mentioned that the concentration levels shown in FIG. 4 represent a percentage of the lower explosive limit (LEL) level for the gas represented by the table. The very use of percent LEL level implicitly performs the conversion from percent concentration by volume to percent LEL.

When the analysis routine of the present embodiment is performed, the second normalized values from the 3.25, 3.35 and 3.4 micron channels (called channels 1, 2 and 3 herein) are read from memory 49 and compared with the values stored in the signature tables. The analysis involves assuming a gas of interest and comparing the current detected values with the signature values for the assumed gas. When the detected values substantially match a row of signature values associated with the same concentration both the gas and concentration are known and appropriate display data is sent to display 45. A match may require that the signature values in the table need to be interpolated. When the current detected values do not substantially match any row of signature values, even with interpolation, for the assumed gas, another gas is assumed and the comparison is again performed until a match is found. Advantageously, the number of signature tables to be compared for any given detected gas may be reduced by grouping gases having a signature with common traits. For example, each gas of interest may be assigned to a subgroup of gases according to the sequence of attenuation in the three detection channels, i.e., 3.25, 3.35 and 3.40 micron. If the three detection channels are respectively numbered 1, 2 and 3, there are six possible subgroups arranged by attenuation. These groups would be 1-2-3, 1-3-2, 2-1-3, etc. Bivinyl would be in the 1-2-3 subgroup; ethane would be in the 2-3-1 subgroup; propane in the 3-1-2 subgroup and so forth. Methane, which absorbs substantially equally in all channels would be in all of the subgroups. When subgroups are used by the analysis routine, the rank order of attenuation in the detection channels is identified from the current values and the rank order defines the subgroup of gas signature tables for complete analysis. That is, if the selected subgroup, e.g., 1-2-3, includes only three gases, then the analysis routine needs only to compare the current values with the signature tables of the three gases in the 1-2-3 subgroup. In the present description a match of within ±5% LEL is considered a substantial match.

In some situations the detection apparatus may not be able to exactly identify a gas present in the atmosphere. Such could happen when the gas signature table for an unknown gas which is present is not in the apparatus. Similarly, some combinations of gases may mask the actual matches for the individual gases. Even though an exact match may not be possible, it is advantageous to advise the user that a gas is present and that it may be present in an amount at or near its LEL level. The present analysis routine optionally includes the ability to provide such information to the user.

As previously discussed, the gas signature tables are grouped according to the attenuation in the three detection channels. In each group, one gas may be predefined as a default gas. The default gas is the gas exhibiting the lowest absorption in the detection channel exhibiting the highest absorption in the group. For example, in the group 3-1-2 the gas exhibiting the lowest absorptions in detection channel 3 is the default gas. When it is determined by comparison with the signature tables that a tested air/gas mixture cannot be identified, the signature table for the default gas is consulted and the measured absorption is compared with the signature absorptions in the highest absorbing detection channel. As a match can not be found only the largest absorption channel is used to determine the gas concentration. This choice maximizes the margin of safety in dealing with an unidentified or unknown gas.

In certain situations, a relatively large change in gas concentration does not result in a significant change in light absorption. Two such situations are shown in FIG. 6, which presents the absorption measured by a particular detector for a particular gas. At very low concentration levels, as shown at 51, and at high concentrations (shown at 53 ), changes in concentration do not result in significant changes in detected absorption. This may lead to non-representative or unreliable results. Similarly, when a test gas does not exhibit significant absorption in one of the detected channels, the measured absorption in the insignificant channel may not accurately represent gas concentration. In order to improve accuracy, an embodiment of the analysis routine includes a routine for computing a weighted average concentration which minimizes the contribution of possibly non-indicative absorption levels.

Instead of identifying the concentration indicated by a single row of a gas concentration table, such as FIG. 4, the weighted average analysis routine computes a concentration (%LEL) in accordance with the following:

$$\% LEL_{average} = \frac{W_1(\% LEL_1) + W_2(\% LEL_2) + W_3(\% LEL_3)}{W_1 + W_2 + W_3} \quad (1)$$

In Equation 1, the weighting factors $W_K$ are computed by:

$$W_K = \Delta a_K / \% \Delta LEL_K \quad (2)$$

and each subscript K represents one of the detection channels.

In this discussion, the 3.25 micron detector is referred to as 1, the 3.35 detector is referred to as 2, and the 3.40 micron detector is referred to as 3. FIG. 5 shows the computation of the $\Delta a_K$ change of absorption, $\Delta\% LEL$, change of concentration and $W_K$ weighing factor for each of the three detectors 1, 2 and 3 in the example for measured absorptions of 0.005 for detector 1, 0.142 for detector 2 and 0.163 for detector 3.

As in the preceding embodiment, the detector absorption readings are taken and normalized; and the gas is identified by the gas signature tables. In the present example, the gas in question is represented by the FIG. 4. In FIG. 5, each numerical row represents the computation of the values $\Delta a$, $\Delta\% LEL$ and W for one of its three detectors. The measured absorption of channel 1 is 0.005, which falls between the %LEL levels of 50% and 100% (FIG. 4). The computed $\Delta a$ of 0.0053 is then the subtraction of the absorption value 0.0049 corresponding to the 50% row of FIG. 4 from the absorption value 0.0092 corresponding to the 100% row of FIG. 4. The computed value of $\Delta LEL$ for channel 1 is the subtraction of the 50 from 100, which represents the %LEL's above and below the measured absorption in FIG. 4. From the computed values of $\Delta a$ and $\Delta\% LEL$, the value (0.0001) of W, is computed from equation (2). The values for $W_2$ and $W_3$ are then computed as described above. Finally, the computed values are used in equation (1) to calculate the %LEL average, which is displayed on the display 45.

The present apparatus and method works well for normal atmospheric variation. It has been observed, however, that large changes in atmospheric pressure, such as use at high elevations, e.g., 10,000 ft., can significantly impact the accuracy of the system. Accordingly, an additional table (FIG. 7) is stored in memory 49 to provide altitude correction factors. When a system is first placed in service, the altitude of use is entered into the micro processor via the input device 47. Whenever a %LEL computation is completed, the correction factor of the altitude correction table corresponding to the altitude table and is used by multiplication to correct the computed %LEL before display.

In some embodiments it has also been found desirable to correct detection channel signals in response to the temperature of the detectors. The apparatus of FIG. 1 includes an optional temperature sensor 32 such as a thermocouple or thermistor, in thermal communication with the detectors. Periodically, the microprocessor 40 senses the temperature of the detectors from the sensor 32 and uses the temperature reading to adjust the actual values read from the detectors. To this end, memory 49 may store a plurality of tables of the type shown in FIG. 7 which store correction factors in correspondence with each of a plurality of possible detector temperatures. The correction factor corresponding to a currently read detector temperature may then be used to adjust measured detection channel values. Although, a predefined set of temperature correction tables may be adequate for all detection systems of a given type, greater accuracy may be achieved when the temperature correction tables are individually generated for each detection system during manufacture.

Figures 7, 8:
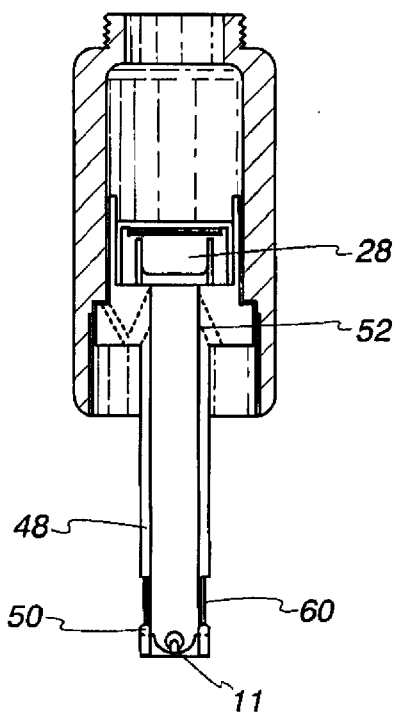
FIG. 7 represents a table of altitude correction factors.
FIG. 8 shows a convection flow gas detection chamber.

FIG. 8 shows a cut away view of an embodiment of a detector assembly shown in FIG. 2. The embodiment of FIG. 8 is best used with a substantially vertical alignment of its major axis. In FIG. 8, similar components have the same reference numerals as in FIG. 2. In FIG. 8, the chamber 48, which is substantially vertically arranged, includes light source 11 providing light power through a gas to be tested to a detector assembly 28. A heating device 2, which is electrically powered by a source (not shown) creates a convection flow of ambient gas through the chamber 48 by drawing gas into input ports 50 and expelling the gas at the top of the chamber through ports 52. Not only does the heating cause convective flow, but by heating its gas slightly, it reduces the risk of condensation within the chamber.

Figure 9:
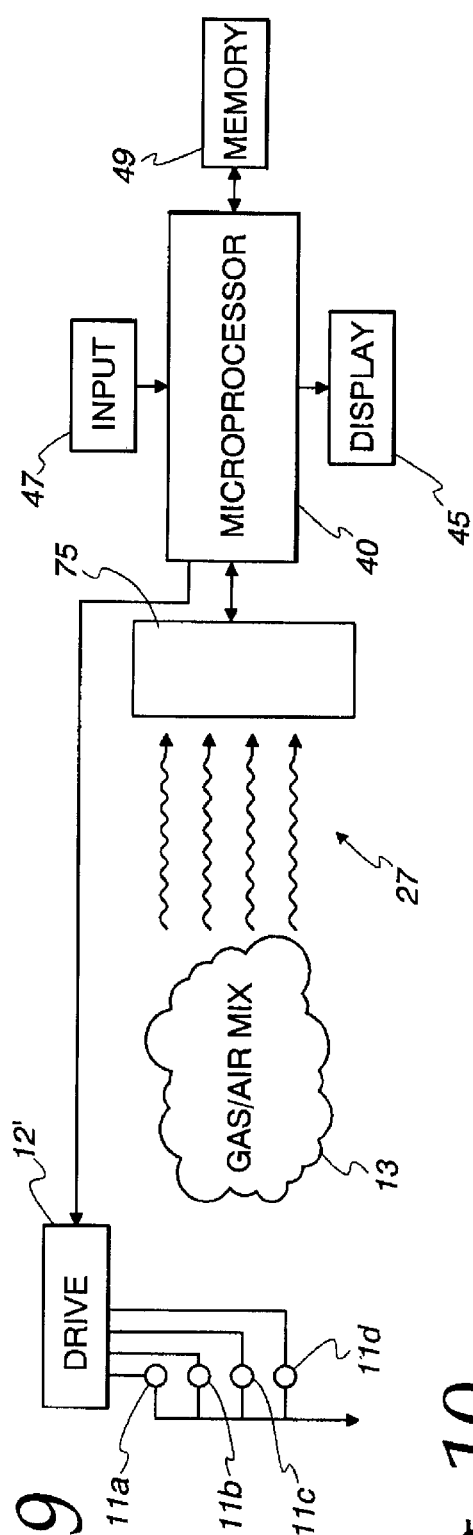
FIG. 9 shows an embodiment having multiple light sources.

The analysis system and method disclosed herein uses light absorption in a plurality of detection channels to identify possible gases of interest. In the preceding embodiments, the detection channels are constructed using a single light source 11 and a plurality of narrow band light detectors. FIG. 9. shows another apparatus for creating a plurality of detection channels. A plurality of narrow band light source 11a, 11b, 11c and 11d each project light through the air/gas mixture under test to a single wide band detector 75. The light sources are turned on and off one at a time under synchronizing control from the microprocessor 40. Output signals from the detector 75 can thus be associated with the four possible detection channel bandwidths one at a time. The output signals from detector 75, as properly matched to the individual detection channels are then analyzed as previously described to identify gases and LELs. In a similar method to the just described time-multiplexed modulation of multiple narrow band light sources a similar set of light sources can also be frequency multiplexed to achieve the same purpose, as is well known in the art. Narrow band mid-IR light emitting diodes could be used in such multiplexed gas sensors.

Figure 10:
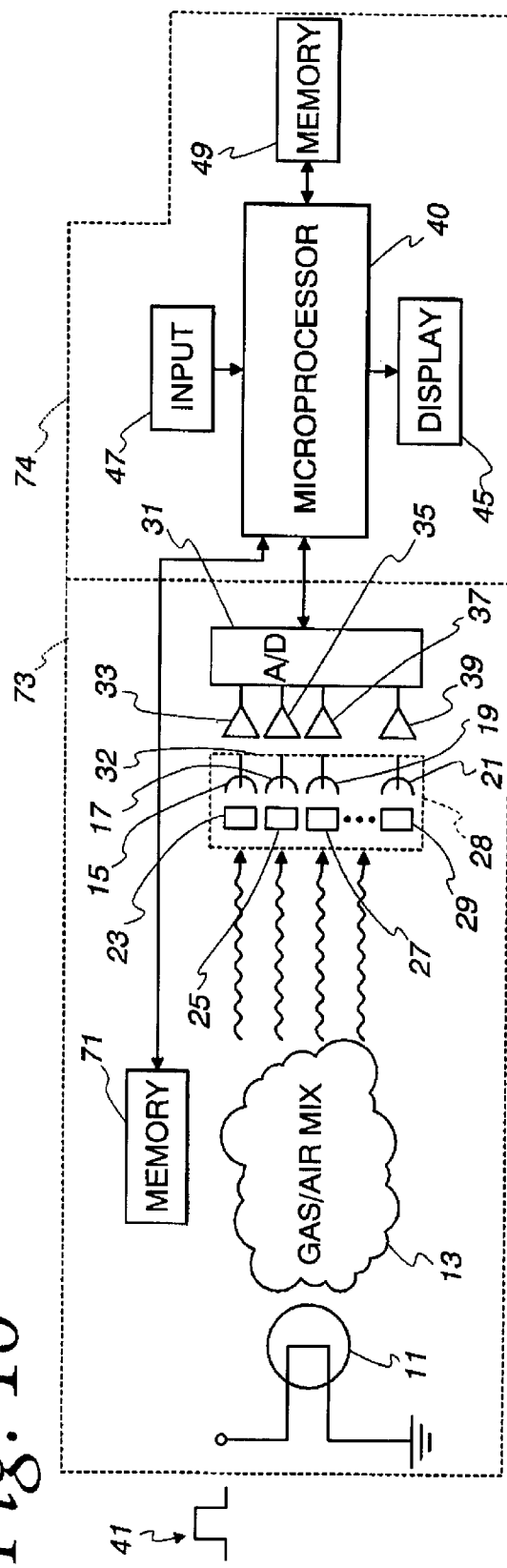
FIG. 10 shows an apparatus having a changeable measuring head.

FIG. 10 illustrates a physical embodiment of the overall test system. In the embodiment of FIG. 10 the apparatus consists of two connectable units. A controller unit 74 includes the processor 40, memory 49, input device 47 and display 45. A measuring head unit 73 includes the apparatus for defining a plurality of detection channels, e.g., the light source filters and detectors, and a memory 72 storing data, such as signature tables, for the detection of specific gases. When a known set of gases is to be tested for, the measuring head 74 for those gases is selected and connected to the control unit 74. During the start-up routine for the microprocessor, the data from memory 72 is read into the control unit 74 for storage and use as above described. Construction in this way permits a single control unit to be shared by multiple measurement heads to allow testing different sets of gases at different times.

The preceding embodiments discussed reference channel detection and three active detection channels. The reference channel detection may be used as described above to identify decreased output by the light source which can be used to adjust detected output levels. It is possible, however, to encounter an air/gas mixture which includes a gas having absorption in the frequency band of the reference channel. When the reference channel is substantially at 3 micron, the presence of acetylene, for example, will result in reduced reference readings which do not indicate reductions in light output. In order to take additional advantage of the reference channel, a seventh group of signature tables may be created to store signature tables containing expected detector output signal levels for gases exhibiting absorption in the reference channel band. The signature tables in the seventh group are distinguished from the other six groups by the fact that all the signature table entries for absorption are greater than unity. While absorption greater than unity is not possible in the physical world, the greater than unity numbers are due to the second normalization step that divides the absorption in the three active channels by the corresponding number of the reference channel.

The preceding embodiments are merely illustrative of the principles of the present invention and many variations may be devised by those skilled in the art without departing from the scope of the invention. For example, although the embodiments discuss explosive levels of gases the present system will function to measure other gas concentrations such as toxicity to humans.

What is claimed is:

1. An apparatus for detecting and measuring gases to be tested, comprising:
    a chamber for receiving an air/gas mixture to be tested;
    a detection channel apparatus comprising one or more light sources for directing light through the air/gas mixture to one or more light detectors to define a plurality of detection channels each responsive to a predetermined portion of the bandwidth of light passing through the air/gas mixture and for generating signals representing an amount of light received for each bandwidth portion;
    a memory storing a plurality of gas signature tables one for each of a plurality of gases to be identified and each signature table comprising a plurality of signature values representing signals to be received from the detection channels at a plurality of air/gas concentrations and further representing gas concentration levels corresponding to a percentage of the lower explosive limit level for each gas; and
    a programmed controller for receiving the signals from the plurality of detection channels, for comparing the received signals with the gas signature tables stored in the memory to identify a gas and the concentration of the identified gas, and for determining whether the concentration of the gas is at or near a lower explosive limit level.

2. The apparatus of claim 1 wherein the detection channel apparatus comprises
    a light source for directing light through the air/gas mixture; and
    a plurality of detectors each for receiving a predetermined portion of the bandwidth of light passing through the air/gas mixture and for generating signals representing an amount of light received.

3. The apparatus of claim 2 comprising a multiplexed analog to digital converter connected to receive signals from the plurality of detectors and apparatus for periodically sampling digital values from the analog to digital converter.

4. The apparatus of claim 1 wherein the memory comprises storage means for storing normalizing values representing the value of detection channel signals when no gas to be tested is present and the controller comprises an apparatus for normalizing detection channel signals when a test gas is expected by dividing the detector signals by the normalizing values.

5. The apparatus of claim 4 comprising means for initiating a start-up routine by the controller in which normalizing values are identified from the detection channel signals and stored in the memory.

6. The apparatus of claim 1 comprising a display connected to the controller for displaying an indicator of at least one gas present and the concentrations of the displayed gas.

7. The apparatus of claim 2 wherein the detectors each comprise a light filter having a predetermined center frequency and bandwidth and circuitry for producing a signal representing the amount of light in the frequency band defined by the filter.

8. The apparatus in accordance with claim 7 comprising at least a first infrared detector having a center wavelength substantially equal to 3.25 microns and a bandwidth substantially equal to 0.04 microns, a second infrared detector having a center wavelength substantially equal to 3.35 microns and a bandwidth substantially equal to 0.04 microns and a third infrared detector having a center wavelength substantially equal to 3.40 microns and a bandwidth substantially equal to 0.04 microns.

9. The apparatus of claim 8 comprising a fourth infrared detector having a center wavelength substantially equal to 3.00 microns and a bandwidth substantially equal to 0.4 microns.

10. An apparatus in accordance with claim 1 wherein the chamber comprises a gas input port and a gas output port, and an apparatus for causing gas flow through the chamber between the input port and output port.

11. An apparatus in accordance with claim 10 wherein:
    the output port is arranged above the input port; and
    the apparatus for causing gas flow is a heating apparatus.

12. The apparatus in accordance with claim 11 wherein the heating apparatus encircles the chamber at a point above the input port and above the one or more light sources.

13. The apparatus in accordance with claim 1 comprising at least one light diffuser between the light source and the detectors.

14. The apparatus in accordance with claim 13 wherein the at least one infrared diffuser comprises a PTFE diffuser having a thickness in the range of 10 microns to 5 millimeters.

15. The apparatus according to claim 13 comprising a first light diffuser in close proximity to the one or more light sources and a second light diffuser in close proximity to the one or more detectors and each of the first and second light diffusers comprise a PTFE diffuser having a thickness from 10 microns to 5 millimeters.

16. The apparatus according to claim 1 comprising a measuring head detachable from the programmed controller, the measuring head including the chamber, the detection channel apparatus and a data store for storing data from which signature tables may be derived for use by the programmed controller.

17. The apparatus according to claim 16 wherein the data store of the measuring head stores data describing signature tables for a set of gasses to be identified by detection channel signals from the detection channel apparatus of the measuring head.

18. The apparatus according to claim 1 wherein the detection channel apparatus comprises a plurality of light sources each for directing light in a predetermined portion of the light band through the air/gas mixture; and
    a detector responsive to light in all of the plurality of portions of the light band for generating detection channel signals.

19. The apparatus according to claim 18 comprising apparatus for turning the light sources on and off one at a time and the controller receives detection channel signals in synchronism with the turn on and turn off of the light sources.

20. The apparatus according to claim 1 comprising apparatus for measuring the temperature of the detectors and the controller adjusts signal values received from the detectors in accordance with the measured temperature.

21. In an apparatus for identifying gases and their concentrations comprising an infrared light source directing infrared light to a plurality of infrared bandwidth specific detectors through a gas under test and a controller, including a memory, for analyzing signals from the detectors representing absorption in a predetermined frequency bands by the gas under test, a method comprising:

storing in the memory a plurality of gas signature tables each representing a specific gas and expected signals from the detectors for various concentrations of the gas and further representing gas concentration levels corresponding to a percentage of the lower explosive limit level for each gas;

reading signals from the detectors to represent the current infrared absorption by a gas under test; and comparing the signals read in the reading step with a plurality of the signature tables to identify the gas under test, to measure the concentration of the identified gas, and to determine whether the concentration of the gas is at or near a lower explosive limit level.

22. A method in accordance with claim 21, comprising reading the signals from the detectors when no gas under test is present and storing normalizing values representing the detector signals when no gas under test is present.

23. A method in accordance with claim 22, comprising reading signals from the detectors when a gas under test is present and dividing the value of the signals so read by a normalizing value.

24. A method in accordance with claim 23 wherein the dividing step comprises dividing the value of signals detected from a given detector by a stored normalizing value corresponding to the same detector.

25. A method in accordance with claim 21 comprising identifying the altitude at which the apparatus is being used and correcting the concentration measured by a stored correction value.

26. A method in accordance with claim 21 comprising measuring the temperature at the detectors and correcting the concentrations measured by a stored correction value.

27. A method in accordance with claim 22 comprising storing in the apparatus a plurality of correction factors, each for a predetermined altitude of use; and identifying to the apparatus the altitude of use to determine an appropriate correction for a measured concentration.

28. A method in accordance with claim 21 comprising:

storing in the gas signature tables a plurality of gas concentration levels and a value representing an infrared absorption level for each detector at each of the plurality of gas concentration levels.

29. A method in accordance with claim 28 comprising identifying a concentration level of a test gas by comparing normalized signal levels from the detectors with the values representing infrared absorption levels from the gas signature tables.

30. A method in accordance with claim 28 comprising identifying a gas concntration level by identifying a concentration level associated with each normalized signal level from the plurality of detectors and averaging the resultant concentration levels.

31. A method in accordance with claim 30 wherein the average of resultant concentration levels is derived by a weighted average method in which each detector level is assigned a weight determined by the change in absorption level divided by the change in gas concentration causing that change in absorption level within the bandwidth of the detector.

32. A method in accordance with claim 31 wherein a first, a second and a third detection channel are used; the weight assigned to each detection channel $W_K$ is computed by:

$$W_K = \Delta a_k / \%LEL_K$$

where $a_K$=a difference in absorption measured by the $K^{TL}$ and $\Delta\%LEL_K$=the concentration level change corresponding to the difference in absorption $a_K$ and the concentration level average $\%LEL_{average}$ is computed by:

$$\%LEL_{average} = \frac{W_1(\%LEL_1) + W_2(\%LEL_2) + W_3(\%LEL_3)}{W_1 + W_2 + W_3}$$

where:

$\%LEL_1$ is the gas signature table concentration level identified by an absorption level $a_1$ for the first detector;

$\%LEL_2$ is the gas signature table concentration level identified by an absorption level $a_2$ for the second detector; and $\%LEL_3$ is the gas signature table concentration level identified by an absorption level $a_3$ for the second detector.

33. A method in accordance with claim 21 comprising assuming the identity of a detected gas when the comparing step fails to identify the gas under test and estimating the %LEL level of the detected gas from a signature table corresponding to the assumed gas.

34. The apparatus in accordance with claim 7 comprising at least a first infrared detector having a center wavelength substantially equal to 3.3 microns and a bandwidth substantially equal to 0.04 microns, a second infrared detector having a center wavelength substantially equal to 3.4 microns and a bandwidth substantially equal to 0.04 microns and a third infrared detector having a center wavelength substantially equal to 3.5 microns and a bandwidth substantially equal to 0.04 microns.

35. The apparatus in accordance with claim 7 comprising at least a first infrared detector having a center wavelength substantially equal to 3.28 microns and a bandwidth substantially equal to 0.04 microns, a second infrared detector having a center wavelength substantially equal to 3.38 microns and a bandwidth substantially equal to 0.04 microns and a third infrared detector having a center wavelength substantially equal to 3.46 microns and a bandwidth substantially equal to 0.04 microns.

* * * * *